United States Patent
Kim et al.

(10) Patent No.: US 9,861,320 B2
(45) Date of Patent: Jan. 9, 2018

(54) METHOD AND APPARATUS FOR EVALUATING EXERCISE CAPABILITY BASED ON HEART RATE

(71) Applicant: SAMSUNG ELECTRONICS CO., LTD., Suwon-si (KR)

(72) Inventors: Younho Kim, Hwaseong-si (KR); Sangkon Bae, Seongnam-si (KR); Byunghoon Ko, Hwaseong-si (KR); Dae-Geun Jang, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/171,428

(22) Filed: Jun. 2, 2016

(65) Prior Publication Data

US 2017/0106241 A1    Apr. 20, 2017

(30) Foreign Application Priority Data

Oct. 15, 2015 (KR) ......................... 10-2015-0144097

(51) Int. Cl.
*A61B 5/00* (2006.01)
*A61B 5/024* (2006.01)
*A61B 5/0245* (2006.01)

(52) U.S. Cl.
CPC .......... *A61B 5/7275* (2013.01); *A61B 5/0245* (2013.01); *A61B 5/02416* (2013.01); *A61B 5/02438* (2013.01); *A61B 5/7239* (2013.01); *A61B 5/746* (2013.01); *A61B 2503/10* (2013.01)

(58) Field of Classification Search
CPC ........ A63B 24/0062; A63B 2024/0065; A63B 2024/0068; A61B 5/024; A61B 5/02438; A61B 5/02416; A61B 5/0245
See application file for complete search history.

(56) References Cited

U.S. PATENT DOCUMENTS

| | | | |
|---|---|---|---|
| 7,366,565 B2 | 4/2008 | Shiga et al. | |
| 2007/0219059 A1* | 9/2007 | Schwartz | A61B 5/0205 482/8 |
| 2013/0231576 A1 | 9/2013 | Tanaka et al. | |

FOREIGN PATENT DOCUMENTS

| | | |
|---|---|---|
| JP | 2003-334269 A | 11/2003 |
| JP | 5540662 B2 | 5/2014 |
| JP | 2014-132934 A | 7/2014 |
| JP | 5776939 B2 | 7/2015 |
| KR | 10-2012-0087117 A | 8/2012 |

* cited by examiner

*Primary Examiner* — Scott Getzow
(74) *Attorney, Agent, or Firm* — NSIP Law

(57) ABSTRACT

Provided is a method and apparatus for evaluating an exercise capability, the method including monitoring a heart rate of a user, setting a detection area to measure an exercise capability of the user based on the monitoring and body information of the user, and detecting a feature point for evaluating the exercise capability from the detection area.

21 Claims, 12 Drawing Sheets

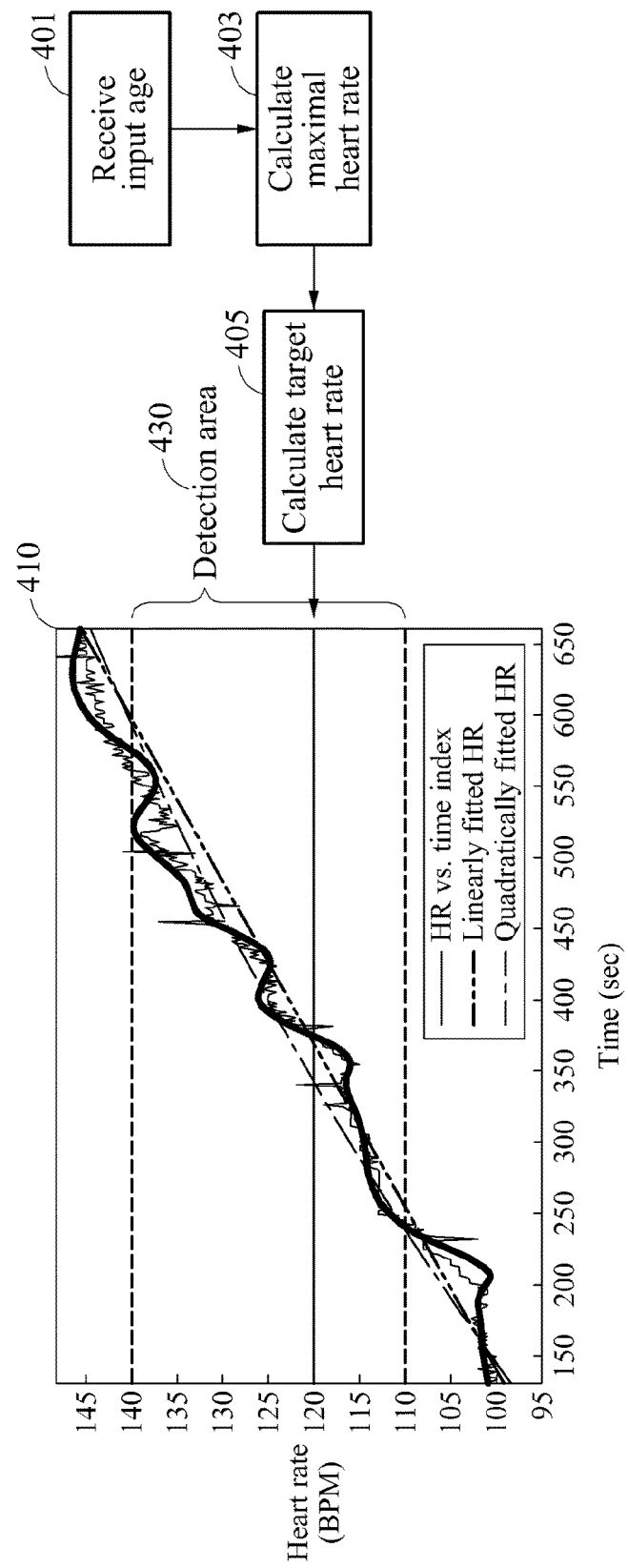

FIG. 8
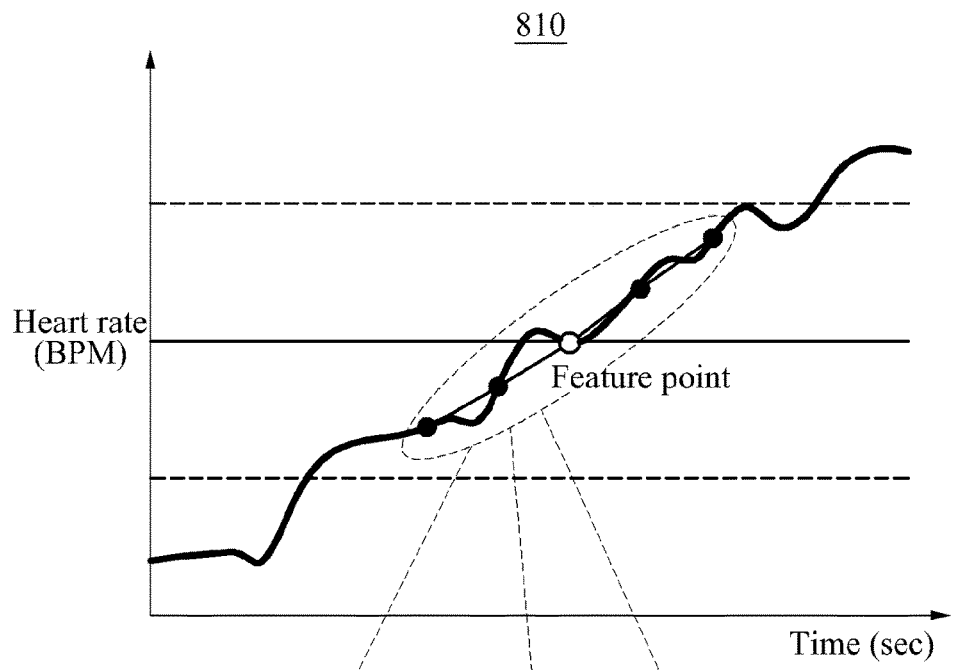
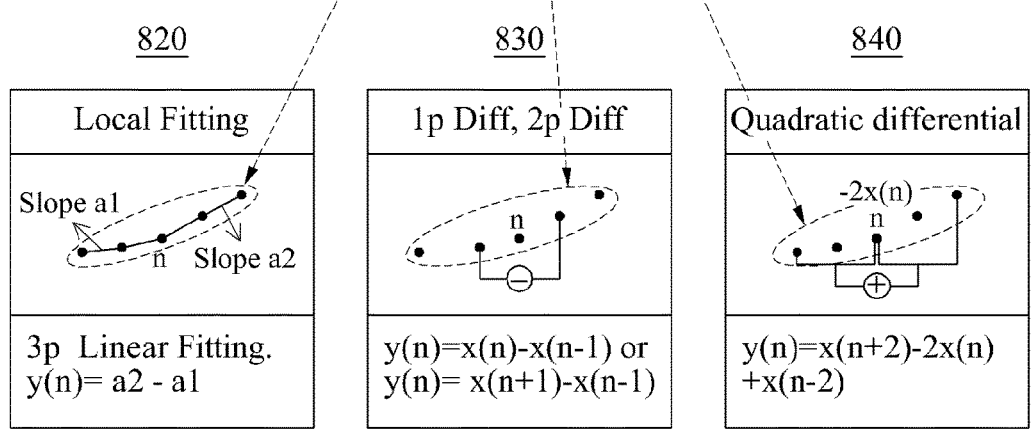

METHOD AND APPARATUS FOR EVALUATING EXERCISE CAPABILITY BASED ON HEART RATE

CROSS-REFERENCE TO RELATED APPLICATION(S)

This application claims the benefit under 35 USC §119(a) of Korean Patent Application No. 10-2015-0144097, filed on Oct. 15, 2015, in the Korean Intellectual Property Office, the entire disclosure of which is incorporated herein by reference for all purposes.

BACKGROUND

1. Field

The following description relates to a method and apparatus for evaluating an exercise capability based on a heart rate.

2. Description of Related Art

A gas analyzer and a blood glucose meter may be used to evaluate cardio-respiratory fitness. Common persons may lack the technical expertise required to handle such devices and the medical knowledge needed for conducting exercise stress tests. Various methods have been developed to conveniently measure a physical fitness level or an exercise capability in daily life. When using a heart rate, which is a physiological characteristic, to evaluate fitness, a physical fitness level and an exercise capability may be evaluated under an assumption of a linear relationship between a heart rate and an exercise intensity.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of evaluating an exercise capability, the method including monitoring a heart rate of a user, setting a detection area to measure an exercise capability of the user based on the monitoring and body information of the user, and detecting a feature point for evaluating the exercise capability from the detection area.

The body information of the user may include at least one of an age or a body mass index (BMI) of the user.

The setting of the detection area may include calculating a maximal heart rate of the user based on the body information, calculating a target heart rate using the maximal heart rate and a goal of exercise, and determining the detection area based on the monitoring and the target heart rate.

The determining may include determining at least one of an upper limit of the detection area, a lower limit of the detection area, or the upper limit through the lower limit of the detection area.

The detecting of the feature point may include determining mean values of heart rates corresponding to time intervals in the detection area, calculating slopes between mean values of heart rates in neighboring time intervals, and identifying a mean value of heart rates corresponding to a greatest slope from among calculated slopes as the feature point.

The calculating of the slopes may include calculating a first slope between a mean value of heart rates corresponding to a first interval in the detection area and a mean value of heart rates corresponding to a second interval neighboring the first interval, and calculating a second slope between the mean value of heart rates corresponding to the second interval and a mean value of heart rates corresponding to a third interval neighboring the second interval.

The detecting may include calculating mean values of heart rates corresponding to time intervals in the detection area, and detecting the feature point based on a difference between a first mean value of heart rates and an adjacent second mean value of heart rates.

The detecting may include calculating mean values of heart rates corresponding to time intervals in the detection area, and detecting the feature point based on a quadratic differential value indicating a change in the mean values of heart rates in the detection area.

The method may include estimating an exercise capability index of the user based on the feature point.

The estimating may include estimating the exercise capability index of the user by applying the feature point to an estimation regression equation.

The exercise capability index may include at least one of a ventilatory threshold or a lactate threshold of the user.

The monitoring may include monitoring a change in a heart rate of the user while the user is performing an exercise with an increasing workload.

In one general aspect, there is provided an apparatus for evaluating an exercise capability, the apparatus including a measurer configured to measure a heart rate of a user, a receiver configured to receive body information of the user, and a processor configured to monitor a change in the heart rate, to set a detection area for measuring an exercise capability of the user based on the change in the heart rate and the body information of the user, and to detect a feature point for evaluating the exercise capability in the detection area.

The processor may be configured to calculate a maximal heart rate of the user based on the body information, to calculate a target heart rate using the maximal heart rate and a goal of exercise, and to determine the detection area based on the change in the heart rate and the target heart rate.

The processor may be configured to set at least one of an upper limit of the detection area, a lower limit of the detection area, or the upper limit through the lower limit of the detection area.

The processor may be configured to determine mean values of heart rates corresponding to time intervals in the detection area, to calculate slopes between mean values of heart rates in neighboring time intervals, and detect a mean value of heart rates corresponding to a greatest slope from among calculated slopes as the feature point.

The processor may be configured to calculate mean values of heart rates corresponding to time intervals in the detection area, and to detect the feature point based on a difference between a first mean value of heart rates and an adjacent second mean value of heart rates.

The processor may be configured to calculate mean values of heart rates corresponding to time intervals in the detection area, and to detect the feature point based on a quadratic differential value indicating a change in the mean values of heart rates in the detection area.

The processor may be configured to estimate an exercise capability index of the user by applying the feature point to an estimation regression equation.

BRIEF DESCRIPTION OF THE DRAWINGS

FIG. 4 illustrates an example of a method of setting a detection area.

FIG. 8 illustrates an example of a method of detecting a feature point.

Figure 1A:
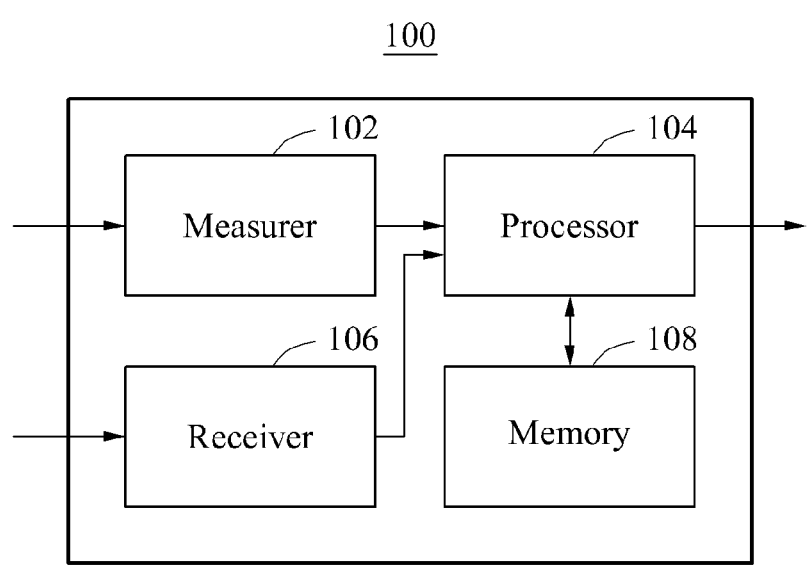
FIGS. 1A and 1B illustrate examples of an apparatus for evaluating an exercise capability.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art after a full understanding of the present disclosure. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

It will be understood that, although the terms first, second, etc. may be used herein to describe various elements, these elements should not be limited by these terms. These terms are only used to distinguish one element from another. For example, a first signal could be termed a second signal, and, similarly, a second signal could be termed a first signal without departing from the teachings of the disclosure.

It will be understood that when an element or layer is referred to as being "on", "attached to", or "connected to" another element or layer, it can be directly on or connected to the other element or layer or through intervening elements or layers may be present. In contrast, when an element is referred to as being "directly on", "directly attached to", or "directly connected to" another element or layer, there are no intervening elements or layers present. Other words used to describe the relationship between elements or layers should be interpreted in a like fashion (e.g., "between" versus "directly between," "adjacent" versus "directly adjacent," "on" versus "directly on").

The terminology used herein is for the purpose of describing particular examples only and is not to be limiting of the examples. As used herein, the singular forms "a", "an", and "the" are intended to include the plural forms as well, unless the context clearly indicates otherwise.

The following example may be applied to evaluate an exercise capability of a user. Examples may be implemented to provide an exercise program suitable for a user or to inform the user of a metabolic disease risk by evaluating an exercise capability of the user based on a heart rate measured from the user in various forms, such as, for example, a personal computer, a laptop computer, a tablet computer, a smartphone, a television, a smart appliance, an intelligent vehicle, a wearable device, and in a smart home system. Example may also be applied to, for example, a healthcare service for the user.

Figure 1B:
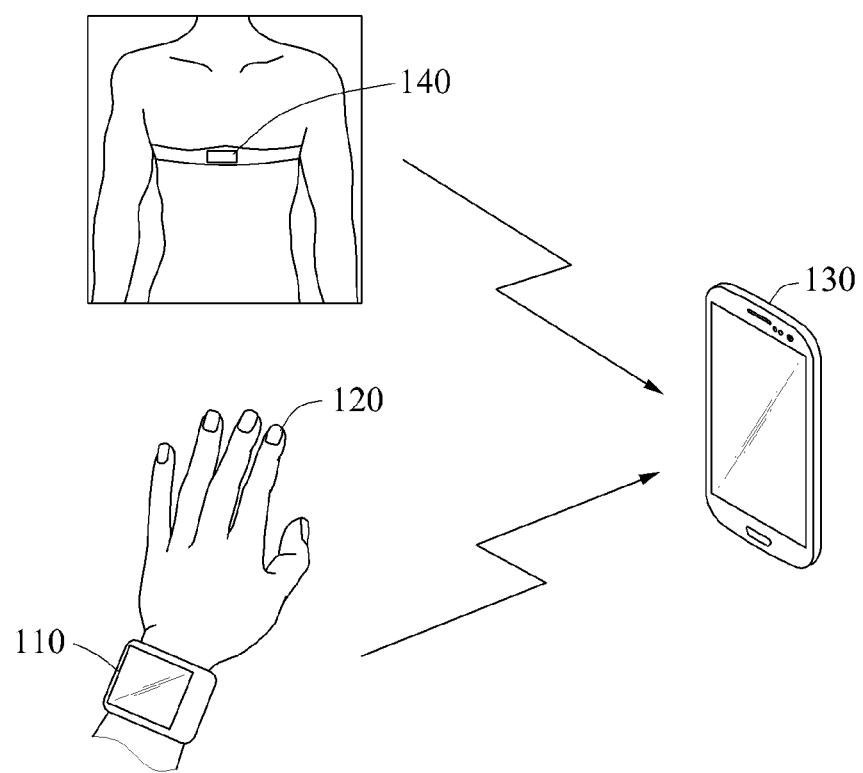

FIGS. 1A and 1B illustrate examples of an apparatus 100 for evaluating an exercise capability. FIG. 1A is an example of a diagram of the apparatus 100 and FIG. 1B illustrates an example of utilizing the apparatus 100.

Referring to FIG. 1A, the apparatus 100 includes a measurer 102, a processor 104, a receiver 106, and a memory 108. The measurer 102, the processor 104, the receiver 106, and the memory 108 communicate with one another.

The measurer 102 measures a heart rate (HR) of a user. The measurer 102 may include sensors, such as, for example, an electrocardiogram (ECG) sensor and a photoplethysmogram (PPG) sensor.

The processor 104 monitors a change in the heart rate of the user, and sets a detection area for measuring an exercise capability of the user based on monitoring and the body information of the user. The processor 104 detects a feature point for evaluating the exercise capability from the detection area.

The processor 104 calculates a maximal heart rate of the user based on the body information, and calculates a target heart rate using the maximal heart rate and a goal of exercise. The processor 104 sets the detection area based on the monitoring and the target heart rate. The processor 104 sets at least one of an upper limit of the detection area, a lower limit of the detection area, and the upper limit through the lower limit of the detection area based on the monitoring and the target heart rate.

The processor 104 calculates mean values of heart rates corresponding to desired (or preset) intervals in the detection area, and calculates a slope between mean values of heart rates corresponding to intervals neighboring each other. The processor 104 detects a mean value of heart rates corresponding to a greatest slope among calculated slopes to be the feature point.

The processor 104 calculates the mean values of heart rates corresponding to the intervals in the detection area, and detects the feature point based on a difference between a first mean value of heart rates and a second mean value of heart rates, adjacent to one another. The processor 104 detects the feature point based on a quadratic differential value indicating a change in the mean values of heart rates in the detection area.

The processor 104 estimates an exercise capability index of the user by applying the feature point to an estimation regression equation.

The receiver 106 receives the body information of the user. The memory 108 stores information, such as, for example, the result of the monitoring, the detection area, and the detected feature point.

In an example, the processor 104 performs at least one method described with reference to FIGS. 2 through 10. The processor 104 executes a program and controls the apparatus 100. A code of the program executed by the processor 104 is stored in the memory 108. In an example, the apparatus 100 is connected to an external source, for example, a personal computer and a network, through an input and output device, thereby performing a data exchange. In an example, the receiver 106 or other communication hardware connects the apparatus 100 to the external source.

At least one of the methods described with reference to FIGS. 1 through 10 is implemented to be in a form of an application executed in a processor of a terminal. As a non-exhaustive illustration only, a terminal described herein may refer to devices such as, for example, a mobile phone, a cellular phone, a smart phone, a wearable smart device (such as, for example, a ring, a watch, a pair of glasses, glasses-type device, a bracelet, an ankle bracket, a belt, a necklace, an earring, a headband, a helmet, a device embedded in the cloths), a personal computer (PC), a laptop, a notebook, a subnotebook, a netbook, or an ultra-mobile PC (UMPC), a tablet personal computer (tablet), a phablet, a mobile internet device (MID), a personal digital assistant (PDA), an enterprise digital assistant (EDA), a digital camera, a digital video camera, a portable game console, an MP3 player, a portable/personal multimedia player (PMP), a handheld e-book, an ultra mobile personal computer (UMPC), a portable lab-top PC, a global positioning system (GPS) navigation, a personal navigation device or portable navigation device (PND), a handheld game console, an e-book, and devices such as a high definition television (HDTV), an optical disc player, a DVD player, a Blue-ray player, a setup box, robot cleaners, a home appliance, content players, communication systems, image processing systems, graphics processing systems, or any other consumer electronics/information technology (CE/IT) device, or any other device capable of wireless communication or network communication consistent with that disclosed herein.

In an example, the terminal may also be implemented as a wearable device, which is worn on a body of a user. In one example, a wearable device may be self-mountable on the body of the user, such as, for example, a watch, a bracelet, or as an eye glass display (EGD), which includes one-eyed glass or two-eyed glasses. In another non-exhaustive example, the wearable device may be mounted on the body of the user through an attaching device, such as, for example, attaching a smart phone or a tablet to the arm of a user using an armband, incorporating the wearable device in a cloth of the user, or hanging the wearable device around the neck of a user using a lanyard.

FIG. 1B illustrates a wearable device 110 and a mobile device 130 configured to have the apparatus 100.

In an example, the apparatus 100 is embedded in the wearable device 110. The wearable device 110 is, for example, a wrist worn device such as, for example, a watch or a bracelet. In an example, the wearable device 110 is provided in a form of a necklace and any other forms. When a user 120 wearing the wearable device 110 performs an exercise, the apparatus 100 evaluates an exercise capability of the user based on a heart rate measured at a wrist of the user 120.

The wearable device 110 including the apparatus 100 may interwork with the mobile device 130 and share data with the mobile device 130. As an example, the heart rate of the user 120 or the exercise capability of the user evaluated by the apparatus 100 is transferred to the mobile device 130.

In another example, the processor 104 is included in the mobile device 103, and the measurer 102 is included in the wearable device 110 and/or a wearable device 140. The wearable devices 110 and 140 are worn on a body part, such as, for example, a wrist, a bicep, or a chest of a user and measure the heart rate of the user 120. The wearable devices 110 and 140 amplify and filter the measured heart rate. The wearable devices 110 and 140 transmit the measures heart rate to the mobile device 130. The apparatus 100 included in the mobile device 130 evaluates the exercise capability of the user based on the heart rate received from the wearable device 110.

The wearable devices 110 and 140 are connected with the mobile device 130 through a wireless link. The mobile device 130 and the wearable devices 110 and 140 may include wireless Internet interfaces, such as, for example a wireless local area network (WLAN) interface, Wi-Fi interface, a digital living network alliance (DLNA interface), a wireless broadband (WiBro) interface, a world interoperability for microwave access (WiMAX) interface, a high-speed downlink packet access (HSDPA) interface, and other interfaces known to one of ordinary skill in the art. The mobile device 130 and the wearable devices 110 and 140 may include short-range communication interfaces, such as for example, a Bluetooth interface, radio frequency identification (RFID) interface, infrared data association (IrDA) interface, a ultra wideband (UWB) interface, a ZigBee interface, and a near field communication (NFC) interface.

The mobile device 130 may be implemented as a terminal described above. The mobile device 130 may be network equipment such as a server. In another example, the mobile device 130 may be a single server computer or at least one server bank or server cloud distributed at different geographical locations.

The mobile device 130 receives various types of biosignals as well as a heart rate through the wearable device 110 or any other a measuring device.

Figure 2:
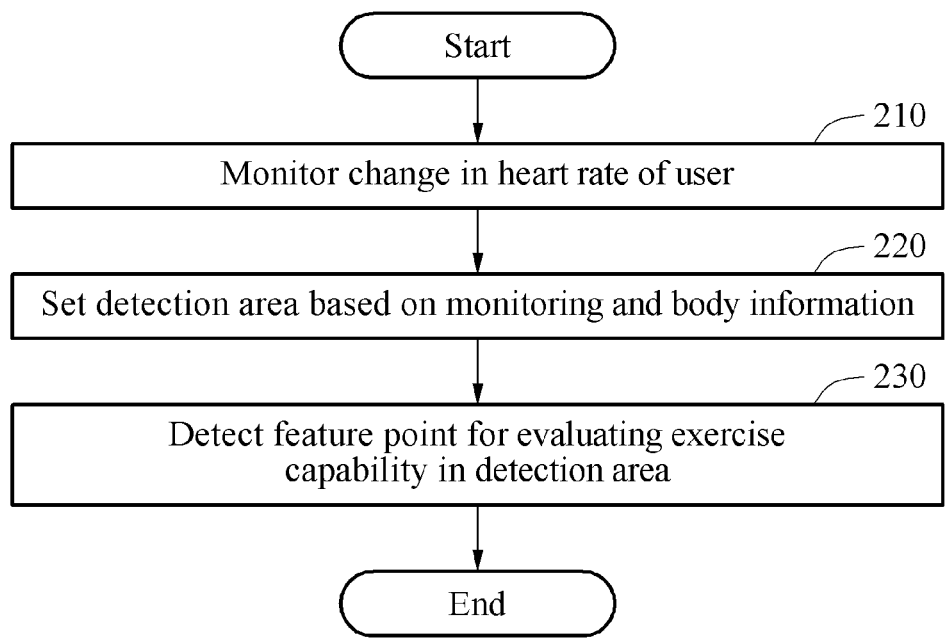
FIG. 2 illustrates an example of a method of evaluating an exercise capability.

FIG. 2 illustrates an example of a method of evaluating an exercise capability. The operations in FIG. 2 may be performed in the sequence and manner as shown, although the order of some operations may be changed or some of the operations omitted without departing from the spirit and scope of the illustrative examples described. Many of the operations shown in FIG. 2 may be performed in parallel or concurrently. In addition to the description of FIG. 2 below, the above descriptions of FIGS. 1A-1B, are also applicable to FIG. 2, and are incorporated herein by reference. Thus, the above description may not be repeated here.

Referring to FIG. 2, in 210, an apparatus for evaluating an exercise capability monitors a change in a heart rate of a user. The apparatus monitors a heart rate of the user while the user is performing an exercise. The apparatus monitors a heart rate sensed from the user while the user is performing a graded load exercise, such as, for example, a treadmill, a bicycle ergometer, a bench step, or a daily exercise in which an exercise load increases, for example, running, jogging, walking, and step climbing.

In an example, the apparatus is a wearable device including a heart rate sensing device or a heart rate apparatus provided in a diversified form such as, for example, a watch type, a bracelet type, a chest type, an in-ear type or a mobile device connected with the wearable device through a wired or wireless communication.

In 220, the apparatus sets a detection area to measure the exercise capability of the user based on the monitoring and the body information of the user. The body information includes information, such as, for example, a gender, an age, a height, a weight, or a body mass index (BMI) of the user. The BMI is obtained by dividing a weight by a square of a height. In an example, a unit of the weight is a kilogram (kg) and a unit of the square of the height is a square meter ($m^2$). In this example, the detection area may have either an upper limit or a lower limit, or both the upper limit and the lower limit. Descriptions related to a method of setting the detection area using the apparatus will be provided with reference to FIGS. 3 through 5.

In 230, the apparatus detects a feature point for evaluating the exercise capability in the detection area. Descriptions related to a method of detecting the feature point using the apparatus will be provided with reference to FIGS. 6 through 8.

Figure 3:
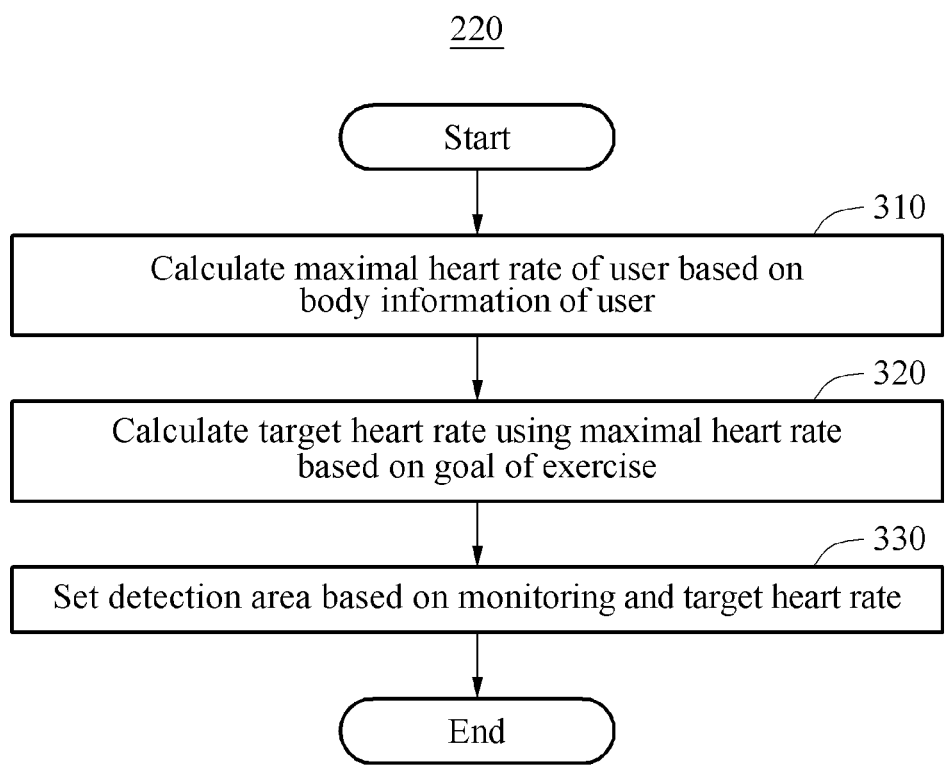
FIG. 3 illustrates an example of a method of setting a detection area.

FIG. 3 illustrates an example of a method of setting a detection area. The operations in FIG. 3 may be performed in the sequence and manner as shown, although the order of some operations may be changed or some of the operations omitted without departing from the spirit and scope of the illustrative examples described. Many of the operations shown in FIG. 3 may be performed in parallel or concurrently. In addition to the description of FIG. 3 below, the above descriptions of FIGS. 1A-2, are also applicable to FIG. 3, and are incorporated herein by reference. Thus, the above description may not be repeated here.

Referring to FIG. 3, in 310, an apparatus for evaluating an exercise capability calculates a maximal heart rate, HR_max, of a user based on body information of the user. In an example, the maximal heart rate is calculated based on an equation, HR_max=220−age.

In 320, the apparatus calculates a target heart rate, Target HR, using the maximal heart rate based on a goal of exercise. The apparatus calculates the target heart rate based on, for example, an aerobic exercise goal. As an example, when the goal of exercise is to reduce weight, the apparatus calculates a heart rate corresponding to about 50% or 60% of the maximal heart rate to be the target heart rate.

In 330, the apparatus sets a detection area based on the monitoring and the target heart rate. Based on an experience or a predetermined rule, the apparatus sets an area of the maximal heart rate, for example, an area corresponding to about 50 to 80% of the maximal heart rate, to be the detection area. In this example, the predetermined area may be an area including the target heart rate.

FIG. 4 illustrates another example of a method of setting a detection area. In FIG. 4, a graph 410 illustrates a change in a heart rate of a user through a monitoring. The operations in FIG. 4 may be performed in the sequence and manner as shown, although the order of some operations may be changed or some of the operations omitted without departing from the spirit and scope of the illustrative examples described. Many of the operations shown in FIG. 4 may be performed in parallel or concurrently. In addition to the description of FIG. 4 below, the above descriptions of FIGS. 1A-3, are also applicable to FIG. 4, and are incorporated herein by reference. Thus, the above description may not be repeated here.

In 401, an apparatus for evaluating a heart rate receives an age input from a user. In 403, the apparatus calculates a maximal heart rate of the user by applying the age to an equation HR_max=220−age. In an example, when the age of the user is 20, the maximal heart rate of the user may be 200 beats per minute (bpm), for example, 220−20=200 bpm.

In 405, the apparatus calculates a heart rate corresponding to about 50% or 60% of the maximal heart rate as a target heart rate. The apparatus calculates, for example, 120 bpm corresponding to 60% of the maximal heart rate, 200 bpm, as the target heart rate.

As shown in the graph 410, corresponding to a fat burn zone, the apparatus sets an area corresponding to 55% through 70% of the maximal heart rate to be a detection area 430 based on the target heart rate, 120 bpm. The apparatus sets an area from 110 bpm to 140 bpm to be the detection area 430.

In another example, a detection area may also be set as an area corresponding to 50% through 80% of a maximal heart rate when a target heart rate is set to be 70% of the maximal heart rate. A percentage of the maximal heart rate to be set as a detection area may be determined based on factors such as, for example, a state of healthiness, an exercise habit, or a physical feature of a user.

Figure 5A:
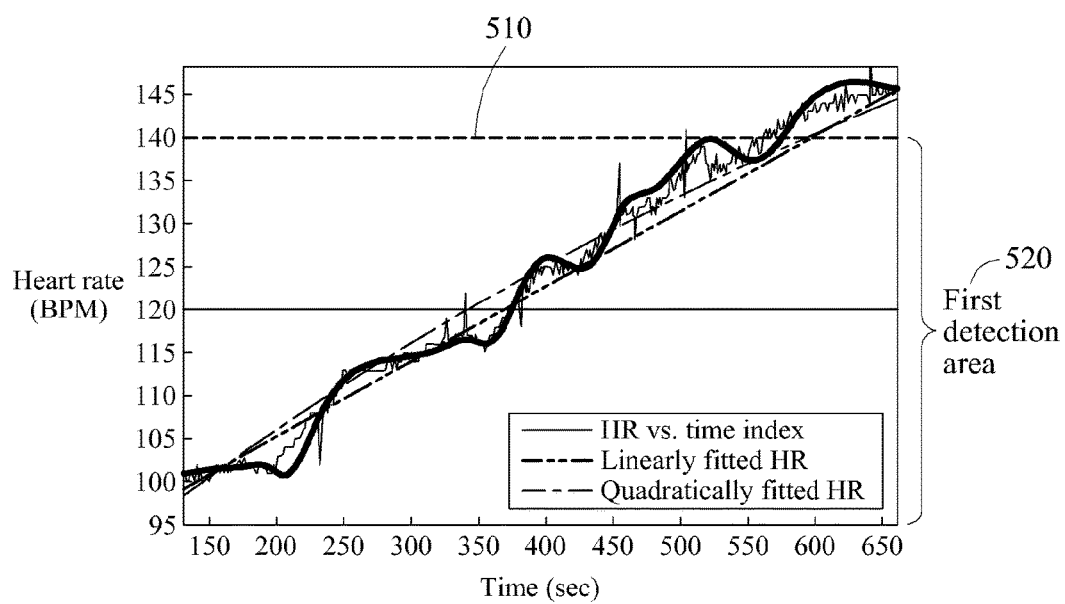
FIGS. 5A and 5B illustrate examples of an upper limit and a lower limit of a detection area.
Figure 5B:
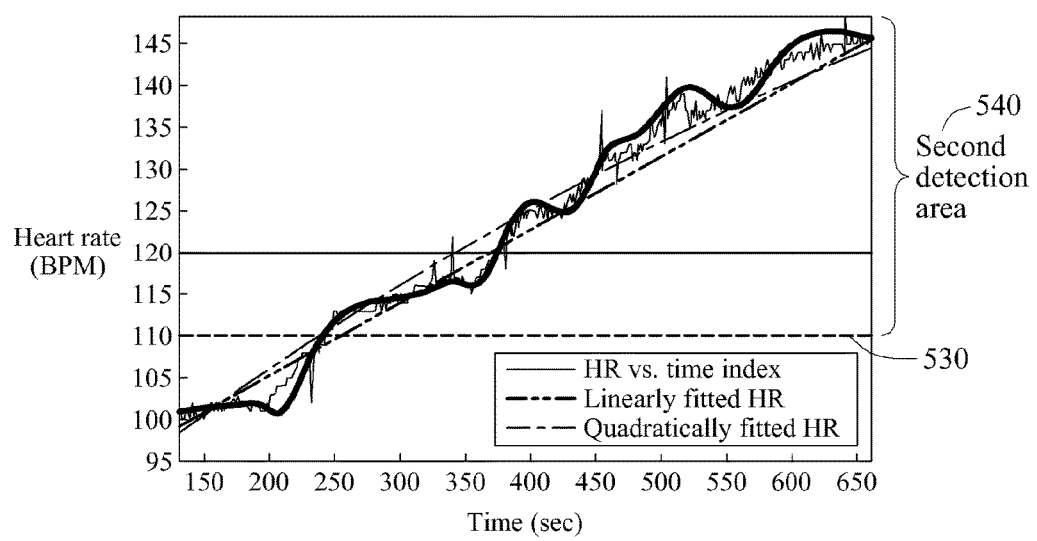

FIGS. 5A and 5B illustrate examples of an upper limit and a lower limit of a detection area. A graph of FIG. 5A illustrates an upper limit 510 of a detection area.

An apparatus of evaluating a heart rate sets the upper limit 510 of the detection area in a result of the monitoring based on a target heart rate. When the upper limit 510 is set, the apparatus detects a feature point for evaluating an exercise capability of a user from a first detection area 520 in the graph of FIG. 5A representing a monitored change in heart rate of the user. In this example, the first detection area 520 is an area from 98 bpm, which is a heart rate corresponding to a point at which the user starts exercising, to 140 bpm, which is a heart rate corresponding to the upper limit 510.

A graph of FIG. 5B illustrates a lower limit 530 of a detection area. The apparatus sets the lower limits 530 of the detection area based on a target heart rate. When the lower limit 530 is set, the apparatus extracts a feature point from a second detection area 540 in the graph of FIG. 5B representing a monitored change in heart rate of the user. In this example, the detection area 540 is an area from 110 bpm, which corresponds to the lower limit 530, to 145 bpm.

Figure 6:
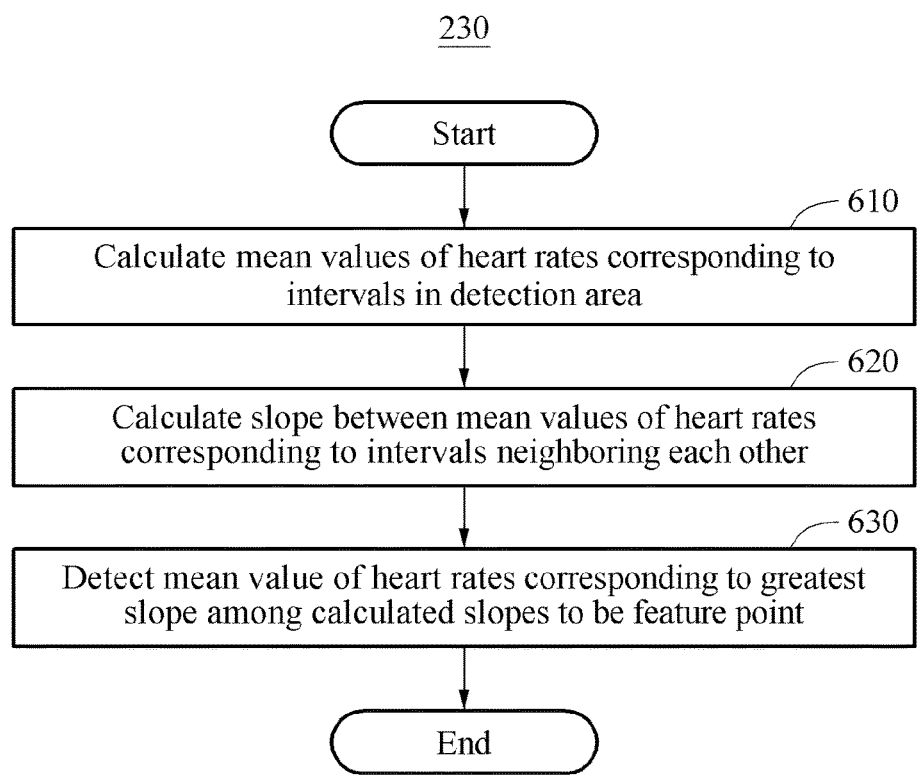
FIG. 6 illustrates an example of a method of detecting a feature point.

FIG. 6 illustrates an example of a method of detecting a feature point. The operations in FIG. 6 may be performed in the sequence and manner as shown, although the order of some operations may be changed or some of the operations omitted without departing from the spirit and scope of the illustrative examples described. Many of the operations shown in FIG. 6 may be performed in parallel or concurrently. In addition to the description of FIG. 6 below, the above descriptions of FIGS. 1A-5B, are also applicable to FIG. 6, and are incorporated herein by reference. Thus, the above description may not be repeated here.

Referring to FIG. 6, in 610, an apparatus for evaluating a heart rate calculates mean values of heart rates corresponding to intervals in a detection area. The apparatus monitors a change in heart rate, for example, at intervals of ten seconds. In an example, the apparatus calculates a mean value of heart rates corresponding to each of intervals of ten seconds in the detection area to be, for example, $HR\_avg(n)=Avg(HR(n-10)\sim HR(n))$, n being a natural number greater than or equal to 10.

The apparatus also calculates mean values of heart rates corresponding to intervals by monitoring a change in heart rate at intervals such as, for example, at intervals of 20, 30, and 5 seconds. When a change in heart rate is monitored at intervals of 30 seconds, the apparatus calculates a mean value of heart rates corresponding to each of the intervals of 30 seconds to be, for example, HR_avg(n)=Avg(HR(n−30) ~HR(n)), n being a natural number greater than or equal to 30 and indicating a time based on a unit of a second.

In 620, the apparatus calculates a slope between mean values of heart rates corresponding to intervals neighboring each other. The apparatus calculates a slope between heart rates corresponding to intervals neighboring each other in the detection area to be, for example, Slope a1=HR_avg(N)−HR_avg(N−1), N being a natural number greater than or equal to 1 and indicating a time interval, for example, 10 or 30 seconds.

In 630, the apparatus detects a mean value of heart rates corresponding to greatest slope among calculated slopes to be feature point. The apparatus obtains a greatest slope, Slope_y(N), among slopes based on, for example, Slope_y(N)=Max(a2(N)−a1(N)), and detects a mean value of heart rates corresponding to the greatest slope to be a feature point.

Figure 7:
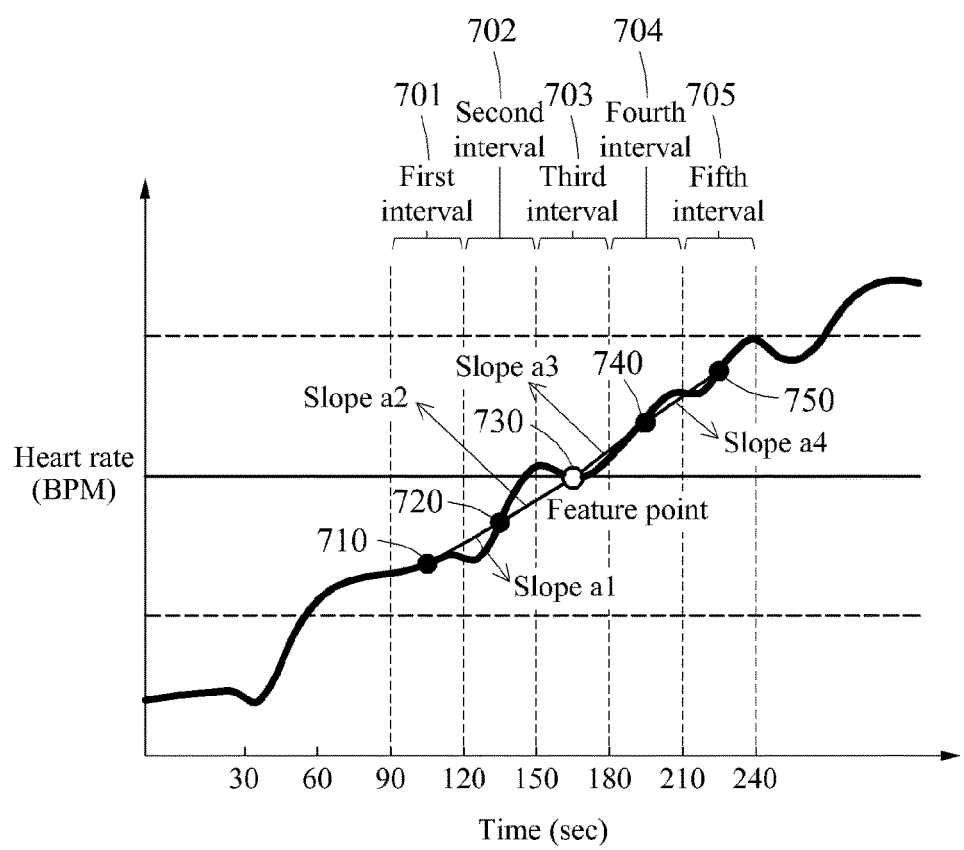
FIG. 7 illustrates an example of a method of detecting a feature point.

FIG. 7 illustrates another example of a method of detecting a feature point. A graph of FIG. 7 illustrates examples of mean values of heart rates corresponding to intervals in a detection area. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. In addition to the description of FIG. 7 below, the above descriptions of FIGS. 1A-6, are also applicable to FIG. 7, and are incorporated herein by reference. Thus, the above description may not be repeated here.

In FIG. 7, an interval corresponding to a detection area is a time interval from 90 to 240 seconds. When an apparatus for evaluating a heart rate monitors a change in heart rate at intervals of 30 seconds, an interval from 90 to 120 seconds is determined to be a first interval 701, an interval from 120 to 150 seconds is determined to be a second interval 702, an interval from 150 to 180 seconds is determined to be a third interval 703, an interval from 180 to 210 seconds is determined to be a fourth interval 704, and an interval from 210 to 240 seconds is determined to be a fifth interval 705.

A mean value of heart rates corresponding to the first interval 701 is a mean value 1, i.e., 710. A mean value of heart rates corresponding to the second interval 702 is a mean value 2, i.e., 720. A mean value of heart rates corresponding to the third interval 703 is a mean value 3, i.e., 730. A mean value of heart rates corresponding to the fourth interval 704 is a mean value 4, i.e., 740. A mean value of heart rates corresponding to the fifth interval 705 is a mean value 5, i.e., 750.

The apparatus calculates a slope between mean values of heart rates corresponding to intervals neighboring each other. The apparatus calculates a slope a1 between the mean value 1, 710, and the mean value 2, 720, corresponding to the first interval 701 and the second interval 702. The apparatus calculates a slope a2 between the mean value 2, 720, and the mean value 3, 730, corresponding to the second interval 702 and the third interval 703. The apparatus calculates a slope a3 between the mean value 3, 730, and the mean value 4, 740, corresponding to the third interval 703 and the fourth interval 704. The apparatus calculates a slope a4 between the mean value 4, 740, and the mean value 5, 750, corresponding to the fourth interval 704 and the fifth interval 705.

In this example, the slope a3 is the greatest slope among the calculated slopes a1, a2, a3, and a4. The apparatus detects the mean value 3, 730, which is the mean value corresponding to the greatest slope, the slope a3 to be a feature value, i.e., heart rate feature point (HRT). Since the foregoing example is based on slopes of at least three points, the method described with reference to FIG. 7 is also referred to as a 3-point linear fitting method or a local fitting method.

For ease and conciseness of description, although FIG. 7 illustrates an example of calculating a mean value based on a change in heart rate at intervals of 30 seconds, this disclosure is not limited thereto. Other intervals, such as, for example, two seconds, five seconds and the like may be used without departing from the spirit and scope of the illustrative examples described. Thus, in an example, a feature point is detected by measuring heart rates at intervals of two seconds, for example, 90, 92, and 94 seconds, and calculating the greatest slope among slopes of the measured heart rates. In another example, the a feature point is detected by measuring heart rates at intervals of five seconds, for example, 120, 125, and 130 seconds, and calculating the greatest slope among slopes of the measured heart rates.

FIG. 8 illustrates another example of a method of detecting a feature point. In FIG. 8, a graph 810 represents a mean value calculated based on a change in heart rate at predetermined time intervals. Points of the graph 810 may correspond to points in each of a block 820, a block 830, and a block 840.

The block 820 indicates an example of the 3-point linear fitting method described with reference to FIG. 7. In an example of the block 820, a feature point, y(n), is obtained based on a difference between a slope a1 and a slope a2.

The block 830 indicates an example of a method of detecting a feature point based on a difference between mean values of heart rates adjacent to one another. An apparatus of evaluating a heart rate calculates mean values of heart rates corresponding to intervals in a detection area, and detects the feature point based on a first mean value and a second mean value of heart rates adjacent to one another. In an example, the difference between the mean value may be a difference between mean values corresponding to directly neighboring intervals, for example, y(n)=x(N)−x(N−1). In another example, the difference between the mean value may be a difference between mean values corresponding to a first time interval and a third time interval, or a second time interval and a fourth time interval, for example, y(n)=x(N+1)−x(N−1). Based on a difference between mean values corresponding to time intervals, the apparatus detects a greatest mean value of mean values corresponding to time intervals directly neighboring one another or spaced in a distance of one time interval to be the feature point.

The block 840 indicates an example of a method of detecting a feature point based on a quadratic differential indicating a change in a mean value of heart rates. The apparatus calculates mean values of heart rates corresponding to intervals in a detection area, and detects a feature point based on a quadratic differential indicating a change in the mean values of the heart rates in the detection area. The apparatus calculates the quadratic differential indicating changes in the mean values of the heart rates based on, for example, y(n)=x(N+2)−2x(N)+x(N−2), and detects a mean value of heart rates corresponding to a largest quadratic differential among the calculated quadratic differentials to be the feature value.

As such, the detecting of the feature point may be performed through a calculation every second in the detection area using heart rate mean values accumulated for 30 seconds, or performed at a interval, for example, 5 seconds or 10 seconds.

In an example, an exercise capability index may be estimated using a final feature point calculated through a combination of the methods described with reference to the graph 810, the block 820, the block 830, and the block 840 of FIG. 8.

Figure 9:
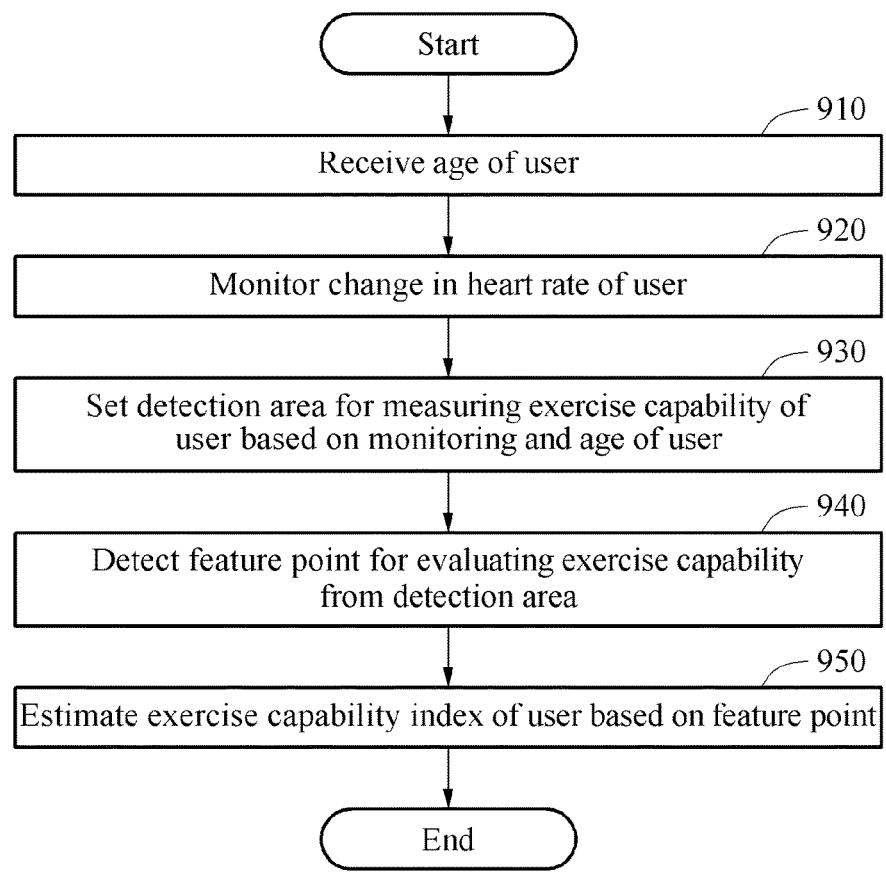
FIG. 9 illustrates an example of a method of evaluating an exercise capability.

FIG. 9 illustrates another example of a method of evaluating an exercise capability. The operations in FIG. 9 may be performed in the sequence and manner as shown, although the order of some operations may be changed or some of the operations omitted without departing from the spirit and scope of the illustrative examples described. Many of the operations shown in FIG. 9 may be performed in parallel or concurrently. In addition to the description of FIG. 9 below, the above descriptions of FIGS. 1A-8, are also applicable to FIG. 7, and are incorporated herein by reference. Thus, the above description may not be repeated here.

Referring to FIG. 9, in 910, an apparatus for evaluating an exercise capability receives an age of a user.

In 920, the apparatus monitors a change in heart rate of the user.

In 930, the apparatus sets a detection area for measuring an exercise capability of the user based on the monitoring and the age of the user.

In 940, the apparatus detects a feature point for evaluating the exercise capability from the detection area. In an example, the apparatus detects the feature point based on the methods described with reference to FIGS. 6 through 8. The above descriptions of FIGS. 6 through 8, is also applicable to FIG. 9, and is incorporated herein by reference. Thus, the above description may not be repeated here.

In 950, the apparatus estimates an exercise capability index of the user based on the feature point. Descriptions related to a method of estimating the exercise capability index of the user will be provided with reference to FIG. 10.

Figure 10:
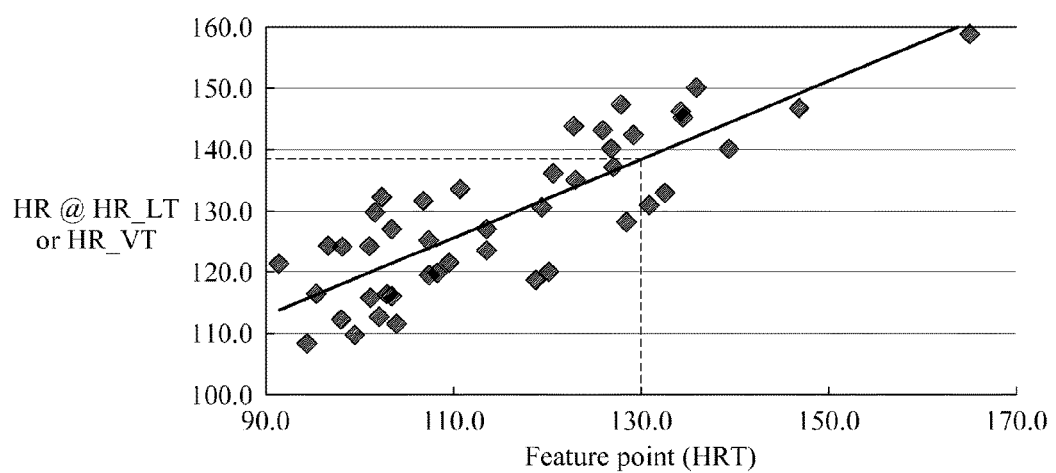
FIG. 10 illustrates an example of a method of estimating an exercise capability index of a user.

FIG. 10 illustrates an example of a method of estimating an exercise capability index of a user.

A heart rate increases proportionally to an exercise intensity, and decreases after reaching an anaerobic threshold (AT) point. Oxygen consumption of muscle, such as, for example, an exercising muscle increases due to an increase in a workload intensity of an exercise being performed. In this example, an energy supply occurs in an anaerobic metabolic process as well as an aerobic metabolic process from a corresponding exercise intensity. As a result of anaerobic metabolism, lactic acid begins to accumulate and an output of carbon dioxide increases. To emit the increased carbon dioxide, body ventilation increases.

An exercise intensity or oxygen consumption corresponding to a point at which such phenomenon starts is also referred to as an anaerobic threshold. The anaerobic threshold includes, for example, a lactate threshold and a ventilatory threshold. The lactate threshold indicates a point at which a lactate density radically increases with respect to an increase in the workload in a relationship between the exercise intensity and the lactate density.

In general, the anaerobic threshold is about 50 to 60% of a maximum exercise intensity. In a case of a long distance runner, the anaerobic threshold increases to be about 80% of the maximum exercise intensity. As such, a heart rate of the anaerobic threshold has a meaningful relationship with, for example, a lactate threshold, LT, and a ventilatory threshold, VT, indicating an exercise capability and a physical strength.

Based on the relationship between the heart rate and the lactate threshold or the ventilatory threshold, the exercise capability may be evaluated using a real time change in the heart rate.

FIG. 10 illustrates a graph representing a relationship between a heart rate feature point HRT and a lactate threshold to heart rate HR_LT or a ventilatory threshold to heart rate HR_VT.

An apparatus for evaluating a heart rate estimates an exercise capability index of a user by applying a feature point detected from a change in heart rate of a user to an estimation regression equation. The exercise capability index may be, for example, a lactate threshold or a ventilatory threshold. The apparatus estimates the exercise capability index, for example, the lactate threshold, by applying the detected feature point to an estimation regression equation, for example, $HR\_LT/HR\_VT = a*HRT + b$ for estimating the lactate threshold to heart rate, a and b being constants greater than 0. In this example, coefficients a and b of the estimation regression equation are differently determined based on an exercise capability index to be estimated.

As an example, when a feature point of a user is 130 bpm, the lactate threshold to heart rate HR_LT is 138 mmol/l as shown in a graph of FIG. 10. The apparatus evaluates an exercise capability of the user based on the estimated exercise capability index, for example, the lactate threshold to heart rate HR_LT of 138 mmol/l. When a maximum load exercise is not performed, the apparatus may also readily evaluate the exercise capability based on an exercise performed to reach a heart rate corresponding to the exercise capability of the user.

The apparatuses, units, modules, devices, and other components illustrated that perform the operations described herein are hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array(FPGA), a programmable logic array, a microprocessor, an application-specific integrated circuit (ASIC), or any other device or combination of devices known to one of ordinary skill in the art that is capable of responding to and executing instructions in a defined manner to achieve a desired result. The processor may denote a type of a computational circuit, such as, for example, a microprocessor, a microcontroller, a complex instruction set computing (CISC) microprocessor, a reduced instruction set computing (RISC) microprocessor, a very long instruction word (VLIW) microprocessor, an explicitly parallel instruction computing (EPIC) microprocessor, a graphic processor, a digital signal processor, or a processing circuit of a different type. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2-4, 6, and 9 that perform the operations described herein are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of evaluating an exercise capability, using one or more processors, the method comprising:
    monitoring a heart rate of a user using a sensor of a wearable device;
    using a mobile device communicating with the wearable device, setting a detection area of a range of heart rates to measure an exercise capability of the user based on the monitoring and body information of the user; and
    detecting a feature point based on a mathematical function of heart rates in intervals within the detection area for evaluating the exercise capability from the detection area.

2. The method of claim 1, wherein the body information of the user comprises at least one of an age or a body mass index (BMI) of the user.

3. The method of claim 1, wherein the setting of the detection area comprises:
    calculating a maximal heart rate of the user based on the body information;
    calculating a target heart rate using the maximal heart rate and a goal of exercise; and
    determining the detection area based on the monitoring and the target heart rate.

4. The method of claim 3, wherein the determining comprises determining at least one of an upper limit of the detection area, a lower limit of the detection area, or the upper limit through the lower limit of the detection area.

5. The method of claim 1, wherein the detecting of the feature point comprises:
    determining mean values of the heart rates corresponding to time intervals in the detection area;
    calculating slopes between mean values of heart rates in neighboring time intervals; and
    identifying a mean value of heart rates corresponding to a greatest slope from among calculated slopes as the feature point.

6. The method of claim 5, wherein the calculating of the slopes comprises:
    calculating a first slope between a mean value of heart rates corresponding to a first interval in the detection area and a mean value of heart rates corresponding to a second interval neighboring the first interval; and
    calculating a second slope between the mean value of heart rates corresponding to the second interval and a mean value of heart rates corresponding to a third interval neighboring the second interval.

7. The method of claim 1, wherein the detecting comprises:
    calculating mean values of the heart rates corresponding to time intervals in the detection area; and detecting the feature point based on a difference between a first mean value of heart rates and an adjacent second mean value of heart rates.

8. The method of claim 1, wherein the detecting comprises:
calculating mean values of the heart rates corresponding to time intervals in the detection area; and
detecting the feature point based on a quadratic differential value indicating a change in the mean values of heart rates in the detection area.

9. The method of claim 1, further comprising:
estimating an exercise capability index of the user based on the feature point.

10. The method of claim 9, wherein the estimating comprises estimating, at a processor, the exercise capability index of the user by applying the feature point to an estimation regression equation.

11. The method of claim 9, wherein the exercise capability index comprises at least one of a ventilatory threshold or a lactate threshold of the user.

12. The method of claim 1, wherein the monitoring comprises monitoring a change in a heart rate of the user while the user is performing an exercise with an increasing workload.

13. The method of claim 1, wherein the detecting of the feature point comprises:
determining mean values of the heart rates between nonneighboring, nonconsecutive time intervals in the detection area; and
detecting a greatest mean value of the mean values as the feature point.

14. A non-transitory computer readable medium comprising a program to control a processor to perform the method of claim 1.

15. An apparatus for evaluating an exercise capability, the apparatus comprising:
a wearable device comprising a measurer including a sensor configured to measure a heart rate of a user; and
a mobile device communicating with the wearable device and comprising
a receiver configured to receive body information of the user; and
a processor configured to monitor a change in the heart rate, to set a detection area of a range of heart rates for measuring an exercise capability of the user based on the change in the heart rate and the body information of the user, and to detect a feature point based on a mathematical function of heart rates in intervals within the detection area for evaluating the exercise capability in the detection area.

16. The apparatus of claim 15, wherein the processor is further configured to calculate a maximal heart rate of the user based on the body information, to calculate a target heart rate using the maximal heart rate and a goal of exercise, and to determine the detection area based on the change in the heart rate and the target heart rate.

17. The apparatus of claim 16, wherein the processor is further configured to set at least one of an upper limit of the detection area, a lower limit of the detection area, or the upper limit through the lower limit of the detection area.

18. The apparatus of claim 15, wherein the processor is further configured to determine mean values of the heart rates corresponding to time intervals in the detection area, to calculate slopes between mean values of heart rates in neighboring time intervals, and detect a mean value of heart rates corresponding to a greatest slope from among calculated slopes as the feature point.

19. The apparatus of claim 15, wherein the processor is further configured to calculate mean values of the heart rates corresponding to time intervals in the detection area, and to detect the feature point based on a difference between a first mean value of heart rates and an adjacent second mean value of heart rates.

20. The apparatus of claim 15, wherein the processor is further configured to calculate mean values of the heart rates corresponding to time intervals in the detection area, and to detect the feature point based on a quadratic differential value indicating a change in the mean values of heart rates in the detection area.

21. The apparatus of claim 15, wherein the processor is further configured to estimate an exercise capability index of the user by applying the feature point to an estimation regression equation.

* * * * *